US00RE37649E

(19) United States
(12) Reissued Patent
Pedrick et al.

(10) Patent Number: US RE37,649 E
(45) Date of Reissued Patent: Apr. 9, 2002

(54) DRAFT TUBE FOR CATALYST REJUVENATION AND DISTRIBUTION

(75) Inventors: Larry E. Pedrick; Charles H. Mauldin; William C. Behrmann, all of Baton Rouge, LA (US)

(73) Assignee: Exxon Research and Engineering Company, Annandale, NJ (US)

( * ) Notice: This patent issued on a continued prosecution application filed under 37 CFR 1.53(d), and is subject to the twenty year patent term provisions of 35 U.S.C. 154(a)(2).

(21) Appl. No.: 09/133,420

(22) Filed: Aug. 13, 1998

Related U.S. Patent Documents

Reissue of:
(64) Patent No.: 5,268,344
Issued: Dec. 7, 1993
Appl. No.: 07/994,215
Filed: Dec. 18, 1992

(51) Int. Cl.[7] ..... B01J 38/58; B01J 38/56; B01J 38/10; C07C 1/04

(52) U.S. Cl. ..... 502/30; 502/31; 502/53; 518/700; 518/709; 518/710; 518/715; 518/719

(58) Field of Search ..... 502/30, 31, 53; 518/700, 709, 710, 715, 719; 208/950

(56) References Cited

U.S. PATENT DOCUMENTS

| | | | | |
|---|---|---|---|---|
| 2,540,706 A | | 2/1951 | Beck et al. | 260/449.6 |
| 2,567,932 A | | 9/1951 | Garbo et al. | 518/709 |
| 2,572,633 A | | 10/1951 | Lanning | 502/53 |
| 2,631,159 A | | 3/1953 | Keith | 518/709 |
| 2,853,369 A | | 9/1958 | Kolbel et al. | 23/288 |
| 2,868,627 A | | 1/1959 | Kolbel et al. | 23/288 |
| 3,629,143 A | | 12/1971 | Reveal | 502/31 |
| 4,670,472 A | * | 6/1987 | Dyer et al. | 518/700 |
| 4,751,057 A | | 6/1988 | Westerman | 422/197 |
| 4,894,205 A | | 1/1990 | Westerman et al. | 422/197 |
| 5,157,054 A | | 10/1992 | Herbolzheimer et al. | 518/700 |
| 5,268,344 A | * | 12/1993 | Pedrick et al. | 502/30 |
| 5,283,216 A | * | 2/1994 | Mitchell | 502/30 |
| 5,288,673 A | * | 2/1994 | Behrmann et al. | 502/30 |

OTHER PUBLICATIONS

"Effects of Fine Bubbles on Flow Patterns in Bubble Column with Suspended Solid Particles," Morooka, et al., J. Chem. Eng. of Japan, vol. 19, No. 6, 1986, pp. 507–512. no month.

(List continued on next page.)

*Primary Examiner*—Alexander G. Ghyka
(74) *Attorney, Agent, or Firm*—Jay Simon

(57) ABSTRACT

Catalyst in a slurry phase reactor is rejuvenated and uniformly distributed in said reactor using a substantially vertical draft tube fully immersed in the slurry which utilizes a rejuvenating gas injected substantially near the bottom of the substantially vertical draft tube whereby catalyst near the bottom of the slurry phase reactor is drawn up the draft tube and discharged from the top of the draft tube near the top of the slurry phase in said reactor.

14 Claims, 6 Drawing Sheets

OTHER PUBLICATIONS

"Gas Holdup and Volumetric Liquid–Phase Mass Transfer Coefficient in Solid Suspended Bubble Column with Draught Tube," Koide, et al., J. Chem. Eng. of Japan, vol. 18, No. 3, 1985, pp. 248–254. no month.

"Application of Airlift Gas–Liquid–Solid Reactors in Biotechnology," Siegel and Robinson, Chem. Eng. Science vol. 47, No. 13/14, pp. 3215–3229, 1992. no month.

"The Catalytic Synthesis of Hydrocarbons from $H_2$/CO Mixtures over the Group VIII Metals," Vannice, J. of Catalysis 37, 449–461, (1975). no month.

"Hydrocarbon Synthesis, Hydrogenation and Cyclization," Emmett, Catalysis, vol. IV, pp. 103–108, Reinhold Publishing Corp. 1956. no month.

"Titania–Supported Metals as CO Hydrogenation Catalysts," Vannice, Journal of Catalysis 74, 199–202 (1982). no month.

"Sparged Loop Reactors," Joshi et al., The Canadian Journal of Chemical Engineering, vol. 68, Oct. 1990, 705–741.

"Reaction Technology in Bubble Columns," Deckwer, Fundamentals of Chemical Technology Process Technology of the Chemical and Related Industries, Otto Salle Veriag Publishers, Sauerlander Publishing 1985, Chapter 1. no month.

"Loop Reactors," Blenke, Adv. Biochem Eng. vol. 13, 1979, pp. 121–124. no month.

* cited by examiner

DRAFT TUBE FOR CATALYST REJUVENATION AND DISTRIBUTION

Matter enclosed in heavy brackets [ ] appears in the original patent but forms no part of this reissue specification; matter printed in italics indicates the additions made by reissue.

FIELD OF THE INVENTION

This invention relates to a process and apparatus for regenerating - rejuvenating and uniformly distributing catalyst in a slurry phase reactor by using a substantially vertical draft tube means, open at both ends, fully immersed in the slurry in said reactor and utilizing rejuvenating gas injected at or substantially near the bottom of said draft tube means through hydrogen gas injection means. Catalyst is drawn up the draft tube means from near the bottom of said reactor under the influence of the rejuvenating gas and ejected from the top of the draft tube means at or below the top of the slurry phase in such reactor. Catalyst reactivation - regeneration is accomplished using the draft tube means by using a rejuvenating gas such as hydrogen. For the purpose of this specification, draft tube means will be referred to variously as draft tube, draft tubes, rejuvenation tube or rejuvenation tubes according to the context of the specification, unless otherwise indicated.

BACKGROUND OF THE INVENTION

Slurry reactors are well known for carrying out highly exothermic, three phase, catalytic reactions. Usually called "bubble columns" these reactors have a liquid phase in which solid catalyst particles are dispersed or held in suspension by a gas phase bubbling through the liquid phase, thereby creating a slurry. These reactors provide improved heat transfer characteristics for the exothermic reaction, with the bubbling gas maintaining the catalyst as a dispersion in the liquid phase.

Bubble column reactors typically have a multiplicity of tubes suspended within a shell-type housing, the tubes being filled with a heat transfer medium, e.g., boiling water, which absorbs the heat generated by the exothermic reaction occurring on the shell side of the tubes in the main body of the housing.

Alternatively the reactor can be of a similar multitube design housed in a common shell-type housing as previously described but wherein the gas and liquid are passed through the multiple tubes which function as the reactor tubes, with effluent being removed from the upper ends of the reactor tubes and heat transfer fluid being passed through the space along the outside surfaces of the reactor tubes. The reactor tubes can be either multiple individual tubes with spaces between adjacent tubes, or multiple bundles of tubes with spaces between adjacent bundles of tubes.

Likewise the entire cross section of the reactor vessel may have a plurality of shafts disposed within it, the bottoms of said shafts being located above the reaction gas inlet but extending a distance above the top surface of the reaction slurry into the gas disengaging spaces so as to create multiple single columns of standing, noncirculating liquid with catalyst suspended and dispersed in said standing liquid. The reaction zone therefor has multiple single columns, said columns having a common bottom reaction gas introduction zone and a common upper gas disengagement space. To insure proper control of the exothermic process additional tubes can be inserted into or between the multiple single columns to function as heat exchangers.

It would be an advance if, in whatever configuration the reaction vessel may take, catalyst within the reaction vessel could be more uniformly distributed and circulated so as to insure more even catalyst aging in the course of the reaction, more effective use of the catalyst by insuring a higher probability that the maximum amount of available catalyst is in the reaction zone to promote the reaction by eliminating stagnant zones of uncirculating, standing catalyst, decreasing mass transfer limitations, and improving heat transfer utilization.

DESCRIPTION OF THE FIGURES

FIG. 5A presents the efficacy of using draft tubes as continuous catalyst rejuvenation tubes using hydrogen as rejuvenating lift gas.

SUMMARY OF THE INVENTION

Figure 1:
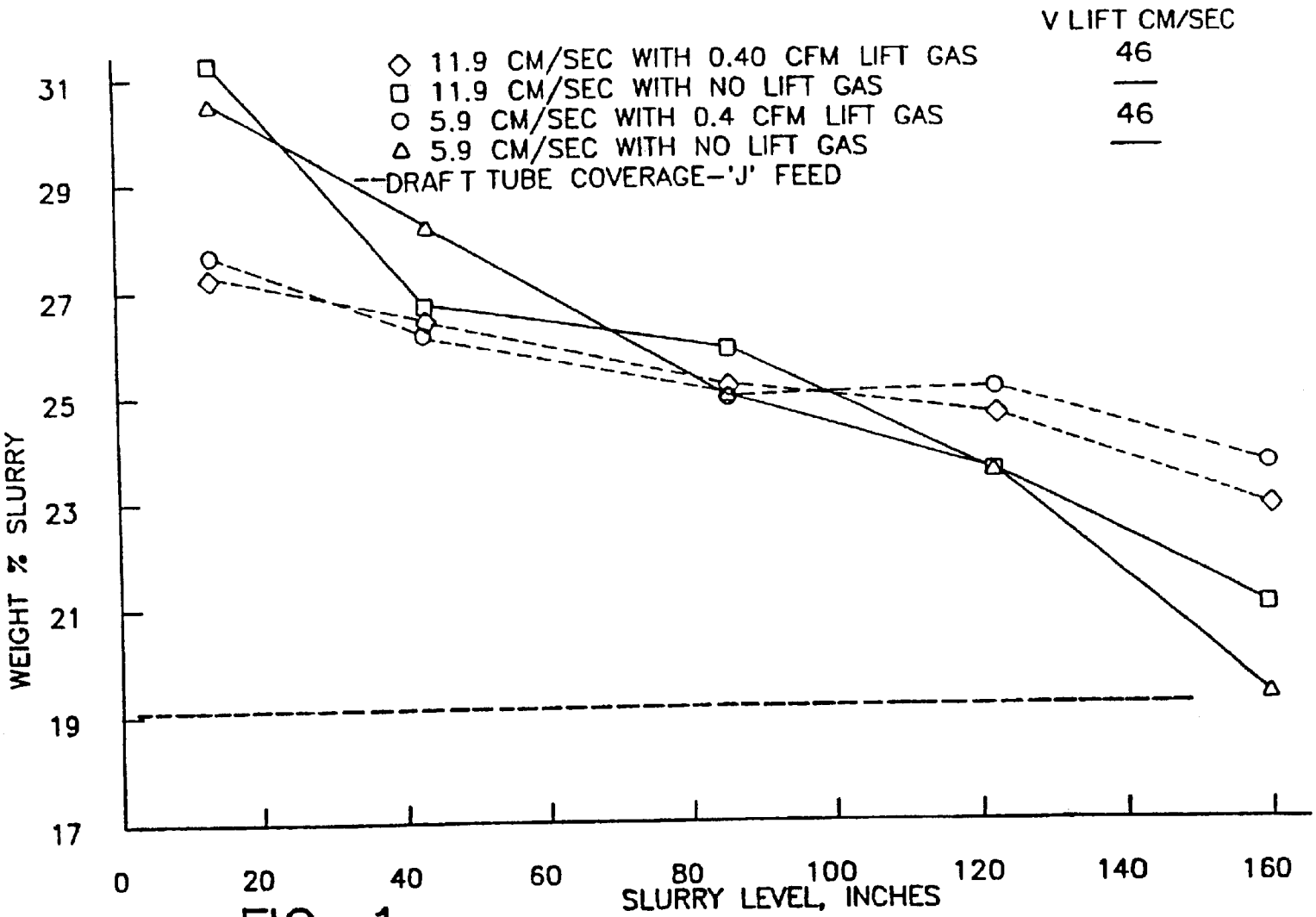
FIGS. 1, 2 and 3 present in graphical form the results of cold mock-up draft tube runs comparing slurry distribution in vessels with and without the use of added lift gas.

Catalysts used in slurry phase reactors, such as hydrocarbon synthesis catalyst used to produce hydrocarbons from synthesis gases, or methanol, which have become reversibly deactivated during use are regenerated - rejuvenated, circulated and uniformly distributed throughout the slurry phase reactor by use of a substantially vertical draft tube, open at both ends, fully immersed in the reaction slurry, the bottom of which draft tube preferably extends to near the bottom of the slurry reactor and the top of which preferably extends to just under the top of the slurry phase, utilizing a rejuvenating lifting gas injected into the draft tube at or substantially near the bottom of said draft tube.

The draft tube is sized in terms of length and diameter so as to insure that flow in said tube is at or above that flow which provides both catalyst lift and catalyst rejuvenation. Velocity of the rejuvenation gas in the draft tube is such that the slurry density in the draft tube is less than the slurry density in the overall reaction vessel. Superficial gas velocities in the tube, therefore, are at least 0.2 to 40 times the superficial gas velocities of the gases in the reactor vessel itself, preferably 0.5 to 20 times, more preferably 3 to 15 times the superficial gas velocities of the gases rising in the reactor vessel.

The draft tubes of the present invention are sized so as to fit within the reaction vessel and are also sized so as to not interfere with the fluid dynamics of the vessel nor with the normal synthesis gas flow within such vessel. These draft tubes occupy, on a cross sectional area basis, as measured in the horizontal plane through the vertical draft tubes, a total of from 0.2 to 10% of the cross sectional area of the reaction vessel, preferably from 0.4 to 8%, more preferably from 0.4 to 5% of the cross sectional area basis of the reaction vessel. Ideally multiple tubes will be employed as to insure maximized catalyst circulation. When multiple tubes are employed no single tube will constitute more than 50%, preferable more than 30%, more preferably more than 10% of the total cross sectional area of the draft tube array.

Narrower diameter tubes are preferred so that fluid dynamics are more easily controlled and so that excessively high superficial gas velocities to achieve adequate lift can be avoided. Within the cross sectional area constraints recited above, tubes having diameters of less than 12 inches, preferably less than 8 inches, more preferably less than 6 inches will be employed in commercial hydrocarbon synthesis vessels.

The length of the tube is important, since when all other conditions, are constant, it is believed the amount of slurry pumped by the draft tube increases as length is increased. Thus the length of the lift tube will be as long as the reactor design allows, i.e., approximately equal to the slurry height in the reactor. The diameter will be set by flow regime considerations in the lift tube and by the amount of slurry that is to be pumped. Successful draft tube operation depends upon the density of the gas-liquid-solid slurry inside the draft tube being less than the density of the gas-liquid-solid slurry in the reactor surrounding the draft tube. The greater the difference is in these two densities, the higher is the velocity in the draft tube.

The density inside the draft tube depends upon the flow regime therein, and that in turn depends upon the draft tube diameter and gas velocity. Furthermore, there is probably some interaction between diameter and velocity. That is to say, an acceptable gas velocity range in a small diameter tube may be different from that in a larger tube, because the differences in densities between the draft tube and reactor slurries will be different for different draft tube diameters, at a given difference in velocity between the draft tube and reactor.

To be effective in catalyst dispersion and rejuvenation, the upward velocity of the fluid in the draft tube must be greater than the settling velocity of the solids, otherwise the solids will not be carried up the draft tube. At the other extreme, too high a gas velocity will cause the flow regime to become annular in which the liquid-solid phase is spread out as an annulus against the wall of the draft tube with the gas passing at high velocity inside the liquid-solid annulus. Between these two extremes of gas velocity, the draft tube goes through an optimum operating region for catalyst dispersion. As the gas rate is increased from a low level, the rate of slurry (liquid+solids) pumping first increases, thereby improving the solids dispersion. As the gas rate is increased further, the pumping rate goes through a maximum and begins to decrease as the gas rate is increased further. This was observed in the mockup of Example 1 (see FIG. 3), discussed in greater detail later, when the gas rate was increased from 0.4 to 0.8 CFM (superficial gas velocity in the tube increased from 46 to 92 cm/sec), the catalyst dispersion was poorer at the higher velocity.

Hydrogen, or such other hydrogen rich gas which may contain inerts such as $CH_4$, light hydrocarbons (e.g., $C_2$–$C_{10}$) etc., but which is substantially free of CO or other hydrocarbon synthesis process feed gases which are reactive with hydrogen, is used in the draft tube as catalyst rejuvenation gas and lifting gas. It has been discovered that hydrocarbon synthesis catalyst which has undergone short term reversible deactivation in the course of the HCS process can be reactivated in the presence of the hydrocarbon synthesis product using hydrogen, said catalyst rejuvenation occurring under the conditions of temperature and pressure similar to those employed for the hydrocarbon synthesis. Catalyst regeneration - rejuvenation using hydrogen or hydrogen containing gas is the subject matter of copending application Ser. No. 949,934 Filed Sep. 24, 1992 in the name of W. N. Mitchell.

To permit the draft tubes to function as catalyst rejuvenation zones the draft tube is fitted at its lower end with gas deflecting means such as a baffle which curtails entry into the tube of synthesis gases yet promotes or facilitates entry of additional liquid and catalyst (slurry). With such synthesis gas influx interdicted, the catalyst and synthesis product liquid present in the tube can be exposed to the hydrogen gas stream injected into the draft tube at or substantially near the bottom of the tube. Because the tube is fully immersed in the reaction slurry, the temperatures and pressures exerted on the contents of the draft tube are those of the synthesis process.

The amount of hydrogen flow into the tube when used as a rejuvenation tube can be throttled such that at the beginning of the regeneration - rejuvenation step flow is low enough so that minimal catalyst is displaced out of the tube through the open top. Flow is maintained at this level for a time sufficient to effect catalyst rejuvenation after which hydrogen flow is increased to lift the catalyst out of the tube to permit a fresh charge of additional catalyst and hydrocarbon synthesis product to be drawn into the tube. Alternatively, hydrogen flow rate is adjusted so that catalyst is continuously being drawn into the tube from the bottom in response to the hydrogen lifting flow; catalyst residence time in the tube is sufficient to achieve the regeneration - rejuvenation of the catalyst by the time any particular catalyst particle has completed its journey to the top of the tube for discharge back into the main reactive slurry.

The extent of the rejuvenation reaction occurring in the continuous mode using the draft tube as the rejuvenation vessel can be monitored by thermocouples placed inside the tube. The measured temperature profile in the rejuvenation tube is compared with the temperature profile in the reactor slurry surrounding the rejuvenation tube, corresponding thermocouples inside and outside the tube being at equivalent heights above the bottom of the reaction vessel. The difference in temperature between the contents of the rejuvenation tube and the reactor slurry is the temperature rise in the rejuvenation tube, which can be used as a measure of the extent of the rejuvenation reaction occurring there. The efficacy of continuous rejuvenation in the rejuvenation tubes depends upon the temperature level in the rejuvenation tube which is controlled to some extent by the temperature in the reactor slurry itself. As previously stated, depending on the level of deactivating species on the catalyst or in the wax, rejuvenation at higher temperatures is preferred.

When catalyst activity is low, indicating that the concentration of the deactivating species in the wax and on the catalyst is high, the amount of reaction that occurs in the rejuvenation tube must also be high, and is evidenced by a greater temperature rise in the rejuvenation tube. When there is only little deactivation, the temperature rise in the rejuvenation tube is proportionally smaller. Hydrogen gas rate to the rejuvenation tube determines the residence time of the reactor slurry in the rejuvenation tubes and is important in determining the efficacy of the rejuvenation. Controlling residence time of the fluids in the rejuvenation tubes is effected by controlling the amount of hydrogen gas being fed to the tube. Too high a rate of hydrogen reduces the residence time in the tube to a point that insufficient time is available for the pre-clean up and clean-up reactions to occur.

The amount of hydrogen passed to the tube in the rejuvenation mode so as to effect sufficient residence time depends on the degree or level of catalyst deactivation, the concentration of deactivating species in the wax present in the slurry, the diameter of the tube, and are all items either within the control of the practitioner or dictated by the conditions of the synthesis reaction itself. Thus, control of hydrogen flow rates to the rejuvenation tube is left to the individual practitioner to set in response to the specific conditions encountered. When used for rejuvenation, the rejuvenation tube can occupy from 0.2 to 10% of the cross sectional area of the reaction vessel.

As disclosed and claimed in copending application Ser. No. 994,219 filed even date herewith in the names of Behrmann and LeViness, degree of catalyst rejuvenation in the rejuvenation tubes can be controlled by independently controlling the rejuvenation temperatures in the rejuvenation tube as compared to the temperature of the surrounding reaction slurry. In many instances this involves conducting the rejuvenation at temperatures higher than those of the surrounding reactor. This control of the temperature in the rejuvenation tubes can be achieved either by increasing the residence time in the rejuvenation tube, so as to take advantage of the exothermic nature of the rejuvenation process itself and thereby increase the temperature, by deliberately introducing heat into the rejuvenation tube, by a combination thereof, or by introducing a cooling medium into the rejuvenation tube, thereby lowering the rejuvenation temperature.

The temperature in the rejuvenation tube should be high enough to react out any entrained and dissolved CO in the lower part of the rejuvenation tube and react deactivating species in the wax and on the catalyst, yet low enough to avoid excessive methane production and hydrolysis of the wax. The rejuvenation temperature in the rejuvenation tubes to achieve effective catalyst rejuvenation may range from about 400° to 500° F., preferably about 420° to 480° F. and more preferably about 440°–470° F. The lower temperatures are effective in those instances in which the catalyst and/or wax contain a minimum of deactivating species. Higher temperatures are needed in those instances when the catalyst and/or wax containing higher levels of deactivating species.

To effectively take advantage of the heat produced by the exothermic nature of the rejuvenation process itself in the rejuvenation tubes, it is preferred that the rejuvenation tube be fitted with insulation means, thus trapping the heat in the rejuvenation tube. This insulation means can take the form of a coating of material of low heat transfer coefficient, such as ceramic. Alternatively the rejuvenation tube can be surrounded by a larger diameter tube with the annular space between the rejuvenation tube and the larger diameter tube surrounding it thus isolating it from the reaction slurry.

Alternately, heat or cooling can be introduced into the rejuvenation tube by means of a separate, independent, controllable heating or cooling means source, such as a steam heat exchanger or electrical heater, run partially or totally up the interior of the rejuvenation tube. When heating, it would be preferable to provide the maximum heat exchange near the bottom of the rejuvenation tube to provide the maximum benefit in increasing the rate and extent of rejuvenation.

When using the independent heat source/heat exchange inside the rejuvenation tube, it is preferable to simultaneously employ an insulating wrap around the rejuvenation tube.

In this and the previous embodiment the heat exchanger extending totally up the inside the rejuvenation tube might serve the purpose of heating the contents of the rejuvenation tube in the lower region and mitigating the temperature rise (i.e. cooling) in the upper region, should reaction rates and heat of reaction be high enough to cause the temperature in the upper regions to rise to undesirable levels.

Ideally catalyst distribution and rejuvenation will be practiced simultaneously using the same draft tubes. When multiple draft tubes are used for catalyst redistribution some of the tubes may be fed rejuvenating gas at a high enough superficial velocity for the purpose of accomplishing both catalyst rejuvenation and redistribution.

When a number of draft tubes are employed as an array, those which are used solely to accomplish catalyst redistribution can be fed lift gas other than just hydrogen or hydrogen containing gas. Non-rejuvenating lift gas can be any gas such as gas feed, tail gases, volatile liquid product, light gaseous hydrocarbons, inert gases such as nitrogen etc., steam. When used for catalyst redistribution the superficial gas velocity in the tube can be in the range of at least 0 to 40 times, preferably 2 to 20 times, more preferably 3 to 15 times the superficial gas velocities of the reaction gases rising in the reactor vessel itself.

As previously stated, the draft tubes are also located in the reaction process zone so as to produce uniform catalyst redistribution through the reaction zone and mitigate or eliminate areas of catalyst stagnation and overcome the natural settling tendency of the catalyst that creates a higher concentration of the catalyst in the bottom of the reactor than at the top. Thus the lower ends of the draft tubes will be placed at or near the bottom of such reaction zones in those areas of low or minimal normal circulation in said zone, preferably from 0.1 to 1.0 foot from the bottom of the reaction zone, more preferably from 0.1 to 0.5 foot from the bottom, most preferably from 0.1 to 0.25 foot from the bottom of the reaction zone. Such stagnant zones exist in bubble column reactors wherein the catalyst is on the shell side in a shell and tube reactor. Bubble column synthesis gas is introduced into such reactor by gas introduction means such as bubble caps at the bottom of the reactor. Due to fluid dynamics stagnant zones are present at the bottom of the reactor surrounding the gas introduction. Catalyst accumulating in those zones is not circulated or lifted by the incoming synthesis gas; such catalyst in effect is lost to the catalytic process. With more advanced gas introduction/distribution means such as multiple cone distributors, stagnant zones of uncirculating, standing catalyst are avoided, but poor catalyst distribution throughout the slurry remains a problem.

The catalyst maldistribution problem revolves around the axial gradient of catalyst concentration. While the energy impacted by the gas bubble tends to disperse the catalyst, gravity causes the catalyst to settle. The degree of dispersion increases with increasing gas velocity, increasing liquid velocity in the upward direction, increasing liquid viscosity, increasing liquid density, and decreasing particle size. For practical conditions encountered in commercial vessels, there is still a large gradient of catalyst concentration from the bottom to the top of the reactor even when multiple cone distributors are used so that there are no stagnant standing zones. It is this gradient which is flattened using the draft/rejuvenation tubes.

In the case of draft/rejuvenation tubes, catalyst is carried by the rejuvenating gas from the high concentration zone in the bottom of the reactor to the low concentration zone at the top of the reactor. Gravity slowly pulls the catalyst particles back to the bottom of the reactor where they are again picked up and lifted to the top.

Siting draft tubes around the e.g., bubble caps in such reactors would result in a siphoning of the catalyst up from the static zone into the draft tube in response to the suction created in the draft tube and the discharge of such formerly static catalyst out the top of the draft tube back into the main reactive slurry mass.

In reactors which are not of the bubble column design but are still of a slurry design employing the gas introduction means described above wherein reaction still occurs on the shell side of any columns in the reactor, similar stagnant zones or concentration gradients exist even though such designs may have associated with them a high degree of back mixing. Eddies can be and are created which create relatively stagnant catalyst zones. Such zones and gradients can also be effectively addressed using the draft tube/lifting gas assembly of the present invention.

As stated, the present invention is of use in hydrocarbon synthesis processes wherein gas, i.e. hydrogen and carbon monoxide, in a ratio ranging from about 0.5 to 4, preferably 0.7 to 2.75, more preferably about 0.7 to 2.5, or other synthesis feed such as methanol, is injected at superficial gas velocities ranging from about 1 to 20 cm/sec through gas injection means such as a bubble cap gas injector grid, or sparger into the main reaction zone in which is located hydrocarbon synthesis product (i.e. hydrocarbon liquids or liquid wax) and catalyst. The gas bubbles up through the reaction zone in contact with the catalyst in the hydrocarbon liquid and is converted into hydrocarbon product. The rising synthesis gas supplies the energy to maintain the catalyst as a dispersion in the hydrocarbon liquid thereby creating a slurry.

Reaction takes place wherever there are synthesis gas, catalyst and suitable reaction conditions, which include pressures ranging from 1 to 100 atmospheres, preferably 10 to 50 atmospheres, more preferably about 15 to 40 atmospheres and temperatures ranging from about 175° C. to about 450° C., preferably about 175° C. to 420° C., more preferably about 175° C. to 300° C.

The slurry phase liquids in which the catalyst is dispersed are those that are liquid at reaction conditions, generally inert, and a good solvent for synthesis gas. Typically, the slurry is the product of the reaction and contains $C_{5+}$ hydrocarbons, usually $C_5$–$C_{100}$ hydrocarbons. Preferably, however, the slurry liquid comprises primarily high boiling paraffins with small amounts of primary and secondary alcohols, acids, esters, or mixtures thereof. Sulfur, nitrogen, phosphorus, arsenic, or antimony heteroatoms are to be avoided since these tend to poison the hydrocarbon synthesis catalyst. Examples of specific slurry liquids are dodecane, tetradecane, hexadecane, octadecane, tetracosane, and the like. Preferred slurry materials are Fischer-Tropsch waxes and $C_{16}$–$C_{18}$ hydrocarbons.

The concentration of solids, including catalyst, in the slurry phase is usually about 10–15% by weight, preferably 20–40 wt % solids.

The hydrocarbon synthesis reaction is highly exothermic and the heat of reaction is removed by a heat transfer material which is either circulating on the shell side of a shell and tube reactor when the reaction takes place in the tube, or through the tubes when the reaction takes place on the shell side. The heat transfer material can be any material having a high heat capacity, whether or not it undergoes a phase change. Preferably the heat transfer fluid is boiling water.

The catalyst employed in the hydrocarbon synthesis process is any catalyst known to be active in Fischer-Tropsch synthesis. For example, Group VIII metals, whether supported or unsupported, are known Fischer-Tropsch catalysts. Of these, iron, cobalt and ruthenium are preferred, particularly iron and cobalt, most particularly cobalt.

A preferred catalyst is supported on an inorganic refractory oxide selected from Groups III, IV, V, VI, and VIII of the Periodic chart of the elements. Preferred supports include silica, alumina, silica-alumina, the Group IVB oxides, most preferably titania (primarily in the rutile form), and generally supports having a surface area of less than about 100 $m^2$/gm, preferably 70 $m^2$/gm and less.

The catalytic metal is present in catalytically active amounts, usually about 100 wt %, (the higher concentrations being typical when iron based catalysts are employed), preferably 2–40 wt %, more preferably about 2–25 wt %. Promoters may be added to the catalyst and are well known in the Fischer-Tropsch catalyst art. Promoters can include ruthenium (when it is not the primary catalytic metal), rhenium, hafnium, cerium, and zirconium, and are usually present in amounts less than the primary catalytic metal (except for ruthenium which may be present in coequal amounts), but the promoter:metal ratio should be at least about 1:10. Preferred promoters are rhenium and hafnium. Useful catalysts are described in U.S. Pat. Nos. 4,568,663; 4,663,305; 4,542,122.

Catalyst particle size is important and particle sizes may range from that which is reasonably separable from the synthesis product to that which is reasonably able to be dispersed in a slurry phase. Particle sizes of 1–200 microns, preferably about 20 to 150 microns meet these requirements. Particles of this size which are easily separable from the synthesis product are those most advantageously benefitted by use of draft/rejuvenation tubes to provide improved dispersion. Particles of this size tend to be more influenced by gravity than are smaller particles which tend to stay in suspension and not settle out.

Catalyst preparation may be accomplished by a variety of techniques, although catalyst preparation does not play a part in this invention and the regeneration - rejuvenation treatment disclosed herein will improve the activity of the hydrocarbon synthesis catalyst however it is prepared.

A typical catalyst preparation may involve impregnation, by incipient wetness or other known techniques of, e.g., a cobalt nitrate salt onto a titania, silica, or alumina support, optionally followed or proceeded by impregnation with a promoter material, e.g., perrhenic acid. Excess liquid is removed and the catalyst precursor dried at 100° C. to 125° C. Following drying or as a continuation thereof, the catalyst is calcined at about 300° C.–500° C. to convert the salt or compound to its corresponding oxide(s). The oxide is then reduced by treatment with hydrogen or a hydrogen containing gas at about 300° C.–500° C. for a period of time sufficient to substantially reduce the oxide to the elemental or catalytic form of the metal. Some prefer an additional cycle of oxidation/reduction. Another, and sometimes preferred method for catalyst preparation is disclosed in U.S. Pat. No. 4,621,072 incorporated herein by reference.

Examples

Example 1

A number of ambient temperature mock-up draft tube demonstrations were performed to demonstrate the ability of draft tubes to redistribute catalyst in a reaction vessel environment. Various runs were conducted in a demonstration apparatus comprising a main vessel having an internal diameter of 5.75 inches in which was located a draft tube of 0.9 inch internal diameter, the draft tube occupying, in cross sectional area about 2.4% of the total cross sectional area of the reactor.

The draft tube was about 12 feet tall and extended from about 0.5 inch above the bottom of the main vessel and ended below the level of the hydrocarbon slurry, which level differed from run series to run series.

The liquid phase of the slurry consisted of predominantly $C_{13}H_{28}$ linear paraffin, which has viscosity, density, and gas hold-up properties similar to the liquid product present under hydrocarbon synthesis (HCS) conditions. Catalyst (12% Co - 1% Re on 94% $TiO_2$-6% $Al_2O_3$, 50% porosity, 4.2 g/cc skeletal density) was used as the solid phase in the slurry.

Figure 2:
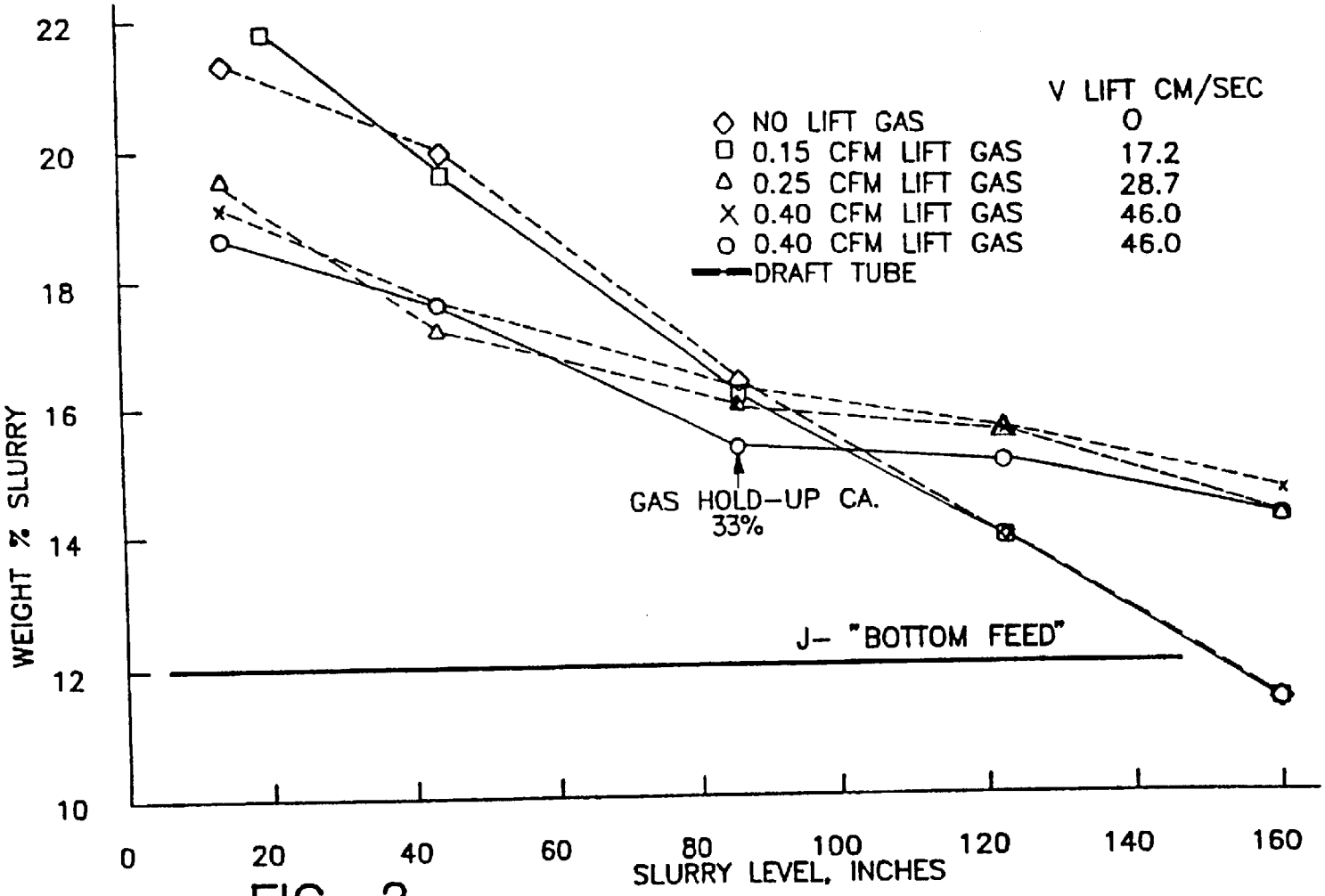
Figure 3:
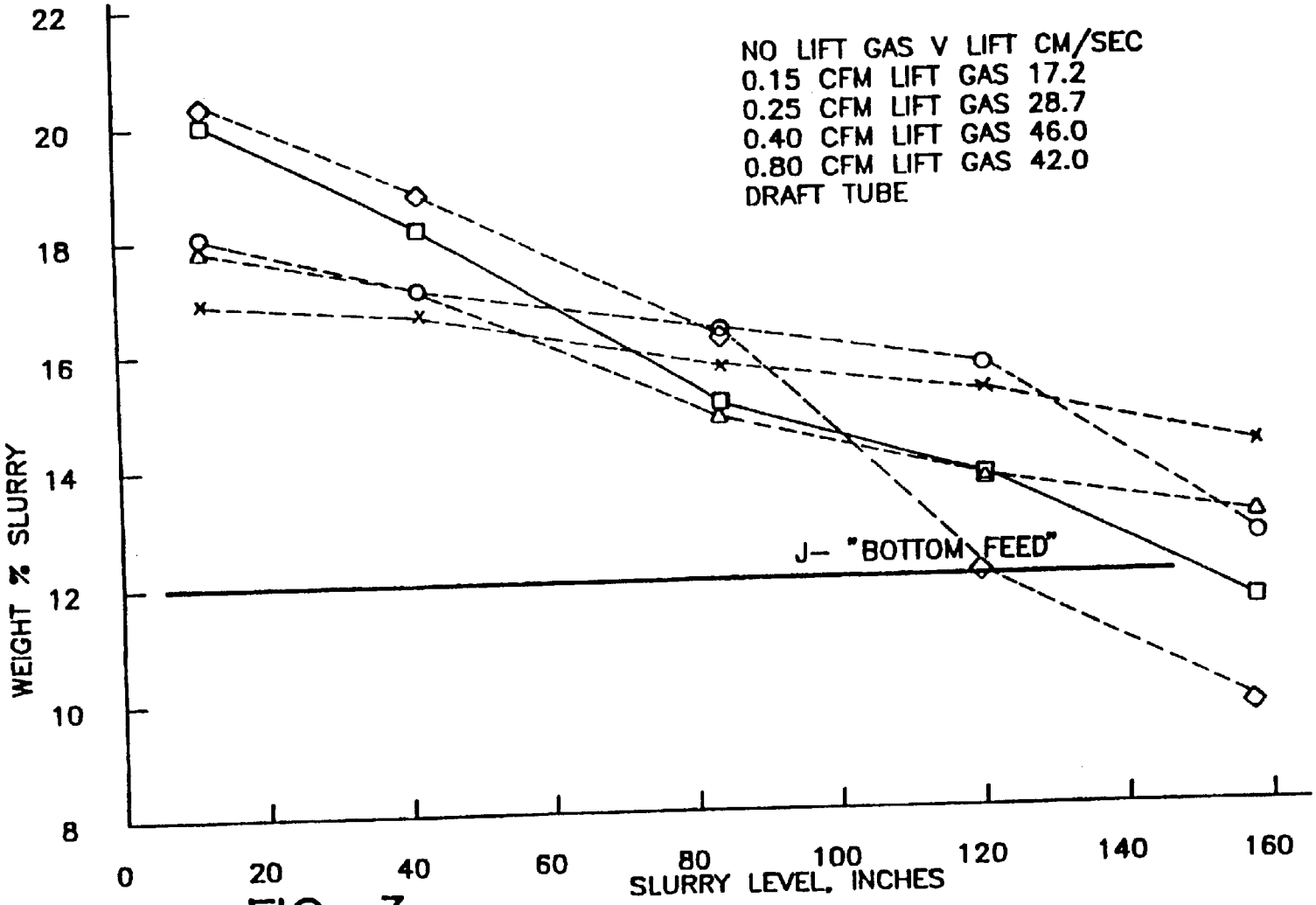

FIGS. 1, 2 and 3 report the results of these demonstrations.

In each figure a series of runs were conducted.

In FIG. 1, there was an average solids concentration of 26 weight percent in the slurry and 33% gas hold up.

In FIG. 2 gas hold up was about 25%, superficial gas velocity was 11.3 cm/sec with a total slurry height of 177 inches.

In FIG. 3 gas hold up was about 25%, superficial gas velocity was 5.6 cm/sec with a total slurry height of 162 inches.

Base line runs were conducted at different gas flow rates (no lift gas) to establish the normal slurry distributions. Additional runs were conducted in which the draft tube was employed using a lifting gas to show the effect on slurry distribution.

In all instances for the particular draft tube used in this example, the runs in which a draft tube was employed using a lifting gas having a superficial velocity greater than at least 1.5 times the superficial velocity of the main feed gas stream, showed an improvement in slurry distribution. When lift gas superficial velocity was in excess of 15 times than the superficial velocity of the gas feed stream, dispersion decreased indicating that dispersion goes through a maximum. The most effective dispersion is represented by the line closest to horizontal, representing almost uniform catalyst distribution across the vessel height. The bottom of the draft tube was in a "J" bottom feed configuration. This configuration operates as a type of baffle to prevent gas from entering the lift tube through its bottom slurry inlet. Physically the "J" bottom feed configuration it achieved by welding two pipes together at a 90° angle. The top half of the horizontal pipe section is removed to allow gas-free solid-liquid slurry to enter the draft tube.

In the following Examples 2 and 3 reference is made to different balances made at different times during the operation of a hydrocarbon synthesis (HCS) pilot plant. The runs used a catalyst comprising 12% Co-1% Re on a support of 94% $TiO_2$-6% $Al_2O_3$, which was activated by reduction in hydrogen at about 350° C. The liquid phase of the slurry consisted of the HCS wax product which is liquid under the reaction conditions of 210°–230° C., 20 atm. pressure. Feed gas composition was about 56% $H_2$-26% CO-13% $CO_2$ - 5% $CH_4$ (by volume). Tail gas was used as feed to the draft tubes when employed. Pure hydrogen was fed to the rejuvenation tubes. An array of cooling water tubes was present in the reactor to remove the heat of reaction. Table I presents the different balances and the conditions employed during each balance, the number of draft tubes and/or regeneration tubes in use, the gas velocities in the tubes, the solids concentration reactor densities and reactor axial temperatures within the reactor slurry at different elevations within the reactor vessel for each balance. Reactor Productivity refers to the volume of CO converted per hour per volume of slurry (catalyst+wax+gas).

TABLE 1

CONDITIONS FOR DRAFT TUBE EXAMPLES
TABULATED RESULTS

| | HCS-PDU Run-Balance | | | | |
|---|---|---|---|---|---|
| | 11 | 47 | 58 | 70 | 41 |
| Draft Tubes in Service | 0 | 0 | 0 | 1–3"φ, 1–4"φ | 2–3"φ, 2–4"φ |
| Rejuvenation Tubes in Service | 0 | 1–3"φ | 1–3"φ | 2–3"φ | 1–3"φ |
| Velocities, cm/sec | | | | | |
| Reactor | | | | | |
| Inlet | 12.3 | 14.3 | 14.6 | 14.3 | 13.7 |
| Outlet | 10.6 | 11.8 | 12.1 | 11.5 | 10.9 |
| Draft Tube | 7.8 | 8.0 | 7.3 | 58.9 | 60.1 |
| Rejuvenation Tubes | 0 | 75.9 | 74.8 | 36.9 | 75.7 |
| Reactor Productivity, Vol CO/Hr/ Vol Slurry | 41 | 61 | 61 | 70 | 69 |
| Solids Concentrations, Lb Catalyst/(Lb Catalyst + Lb Wax) Elevation. Ft. | | | | | |
| 0.23 | 0.4276 | 0.4030 | 0.4518 | 0.4140 | 0.3361 |
| 2.52 | 0.4202 | 0.2820 | 0.3627 | 0.2960 | 0.2275 |
| 5.47 | 0.3340 | 0.2843 | 0.3189 | 0.2462 | 0.2273 |
| 9.41 | 0.2329 | 0.2185 | 0.2380 | 0.2158 | 0.2053 |
| 13.49 | 0.1835 | 0.1965 | 0.1994 | 0.2202 | 0.2095 |
| 20.49 | 0.0969 | 0.1690 | 0.1127 | 0.1624 | 0.2000 |
| 30.47 | 0.0660 | 0.1178 | 0.0969 | 0.1497 | 0.1860 |
| Reactor Densities, Lb/Cu. Ft. Elevation, Ft. | | | | | |
| 0.0–2.5 | 49.27 | 36.39 | 37.65 | 30.29 | 31.13 |
| 2.5–9.8 | 35.53 | 28.54 | 28.74 | 26.56 | 26.10 |

TABLE 1-continued

CONDITIONS FOR DRAFT TUBE EXAMPLES
TABULATED RESULTS

| | HCS-PDU Run-Balance | | | | |
|---|---|---|---|---|---|
| | 11 | 47 | 58 | 70 | 41 |
| 9.8–19.8 | 25.03 | 23.87 | 20.82 | 22.21 | 22.83 |
| 19.8–29.8 | 21.29 | 21.62 | 17.91 | 20.63 | 21.15 |
| 29.8–35.3 | 9.30 | 19.16 | 16.87 | 21.45 | 20.35 |
| 35.3–39.8 | 0 | 4.94 | 1.12 | 1.0 | 1.92 |
| 39.8–48.8 | 0 | 0 | 0 | 0 | 0 |
| Reactor Axial Temperature Profile, ° F. | | | | | |
| Elevation, Ft. | | | | | |
| 1.0 | 415 | 415 | 424 | 424 | 413 |
| 2.0 | 418 | 416 | 425 | 425 | 414 |
| 3.0 | 421 | 417 | 427 | 427 | 416 |
| 4.0 | 422 | 417 | 428 | 427 | 416 |
| 5.0 | 424 | 418 | 429 | 429 | 418 |
| 6.0 | 423 | 417 | 427 | 428 | 417 |
| 7.0 | 424 | 417 | 427 | 428 | 417 |
| 8.0 | 425 | 417 | 427 | 428 | 417 |
| 9.0 | 425 | 417 | 426 | 428 | 417 |
| 10.0 | 425 | 416 | 425 | 428 | 417 |
| 11.0 | 426 | 417 | 426 | 429 | 419 |
| 13.0 | 424 | 417 | 423 | 427 | 417 |
| 15.0 | 424 | 416 | 423 | 428 | 418 |
| 17.0 | 423 | 414 | 421 | 427 | 417 |
| 19.0 | 423 | 414 | 421 | 428 | 418 |
| 21.0 | 423 | 414 | 421 | 428 | 418 |
| 23.0 | 422 | 413 | 419 | 427 | 417 |
| 25.0 | 422 | 413 | 419 | 428 | 417 |
| 27.0 | 422 | 413 | 418 | 427 | 418 |
| 29.0 | 421 | 412 | 417 | 426 | 417 |
| 31.0 | 421 | 413 | 417 | 427 | 418 |
| 33.0 | | 413 | 417 | 428 | 418 |
| 35.0 | | 410 | 414 | 425 | 414 |
| 37.0 | | | | | |
| 39.0 | | | | | |

Example 2

The efficacy of using draft tubes for enhanced catalyst circulation was demonstrated in a hydrocarbon synthesis pilot demonstration unit which is 4 feet in diameter and had a reaction slurry height of about 35 feet.

Balance 11 was made at the start of run, no lift gas was injected into any draft tubes and no rejuvenation tubes were in use.

Between days 6 and 7 in the run (Balance 41), about 25,000 standard cubic feed per hour of HCS product gas was recycled to four draft tubes, two of which were 3" diameter pipe and two of which were 4" diameter pipe, giving a superficial gas velocity of about 2 feet/sec in the draft tubes. In total the 4 draft tubes, having a total cross sectional area of 39.28 sq. inches occupied only 2.17% of the total cross sectional area of the reaction vessel (1809.21 sq. inches). A pair of 3" diameter tubes (14.12 sq. inches) occupied only 0.78% while a pair of 4" diameter tubes (25.12 sq. inches) occupied only 1.39% of the total cross sectional area of the vessel. A pair of tubes made up of only one 3" and one 4" diameter tubes had a total cross sectional area of 19.62 sq. inches and occupied only 1.08% of the total cross sectional area of the vessel.

Referring to Table I "Reactor Densities", a higher density reading indicates a higher catalyst loading. These density readings show that during the measurement period Balance 41 between days 6 and 7 during which the lift gas rate was about 25 KSCF/hr, density readings in the bottom of the reactor fell dramatically and the density reading near the top of the slurry increased as compared to catalyst distribution and density reading reported for Balance 11, no lift gas in use. Furthermore, the four lower densities were very similar while the draft tubes were in service. These density changes were the result of the catalyst being much more uniformly distributed throughout the reactor.

Figure 4:
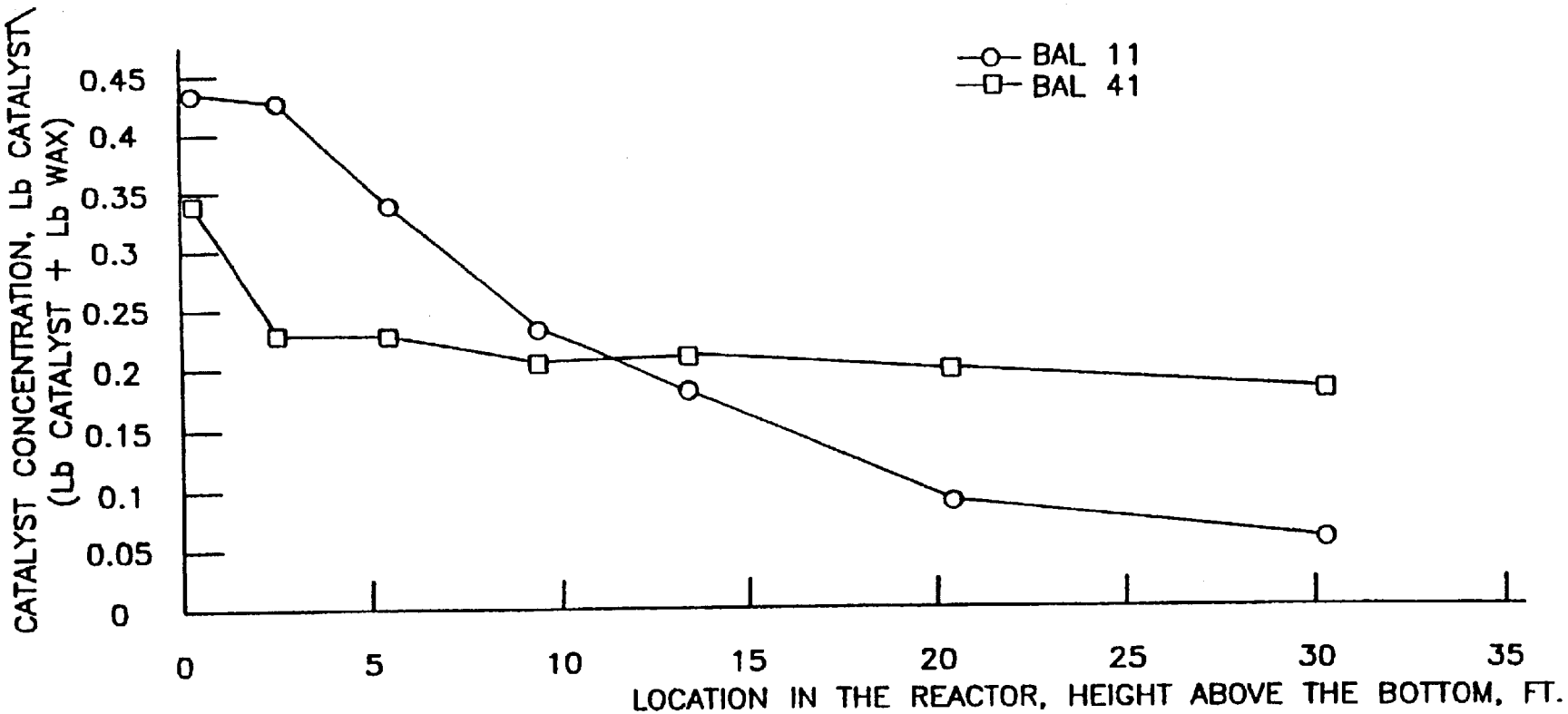
FIG. 4 presents axial catalyst distribution comparisons at specific measurement moments before and during draft tube operation in an operating bubble column reactor (4 draft tubes and one rejuvenation tube in use).

This change in catalyst loading is shown graphically in FIG. 4. This Figure shows the catalyst concentration, expressed as lb catalyst per lb of slurry (catalyst plus wax), plotted against elevation in the reactor. Balance 11, a measurement made at 1.62 days, before the draft tube experiment was carried out, shows a typical catalyst distribution without the draft tubes in which there was almost a 10-fold change in catalyst concentration across the length of the reactor. However, in Balance 41, a measurement made at day 6.41 in the middle of the draft tube experiment, with all 4 draft tubes in use (plus one additional tube of 3" diameter used for in-situ catalyst regeneration (see Example 3)) and at a lift gas superficial velocity of 60.1 cm/sec, the catalyst concentration was nearly uniform from the 2.5- to the 30.5-foot level. The catalyst concentration at the 0.2-foot level was not as dramatically affected because the lower end of the lowest lift tube was positioned at the 0.5-foot level and therefore was not completely effective in lowering the catalyst concentration at the 0.2-foot level. In the region of the reactor over which the draft tube was operating, the catalyst concentration was nearly uniform, thus proving the effectiveness of the draft tube concept.

The draft tube concept was again demonstrated between days 10 and 12 in balance 70. This time only two lift tubes (one 3" and one 4" diameter) and two regenerator tubes of 3" diameter were used with a lift gas superficial velocity of 58.9 cm/sec in each draft tube thus reducing the total lift gas employed by a factor of two. Rejuvenation gas rate was 36.9 cm/sec. Comparison of Balances 70, 47, 58 and 41 shows that the reactor densities were improved nearly to the same extent as when four draft tubes were used. The use of two draft tubes (and two regenerator tubes) Balance 70 definitely improved the catalyst dispersion over that obtained without the draft tubes Balances 58 or 47, but the benefit was not as great as that achieved by four draft tubes plus one rejuvenator tube Balance 41, the total being of greater overall diameter and which occupied a higher percentage of the cross sectional area of the reactor vessel. With four draft tubes, the ratio of the concentration at the bottom of the reactor (2.5-foot level) to that at the top of the reactor (30.5-foot level) was less than 1.3, while with the two draft tubes (plus 2 regenerator tubes) the ratio was 2. The concentration at the very bottom of the reactor (0.2-foot level) was also significantly higher with the two tubes than with the four tubes (42 wt % vs. 33 wt %).

The use of the draft tubes to improve the catalyst dispersion also flattened the axial temperature profile in the reactor. This is shown in the case of four lift tubes and one 3" diameter regeneration tube (balance 41) vs Balances 47 or 58 and for the case of two lift tubes (balance 70 as previously discussed) as compared with balance 58 in which no lift tubes were used (but using regeneration tubes of 3" diameter). Balance 58 data show that without the use of the draft tubes the temperature difference between the top and bottom of the reactor is over 12° F., while the temperature difference when four draft tubes were operated (Balance 41) was actually negative because of the lower temperature in the bottom of the reactor caused by the cooling effect of the incoming gas feed. For Balance 70 with two draft tubes and two rejuvenator tubes in operation there was perhaps a 2° F. difference between the top and bottom of the reactor.

These two examples demonstrate that very modest sized draft tubes occupying less than three percent of the reactor cross section very effectively improve the dispersion of the catalyst. The benefits of improved catalyst dispersion are: (1) reduced mass transfer limitations and thereby improved catalyst utilization, and (2) improved temperature distribution that reduces the selectivity to unwanted lighter products and that improves the utilization of the heat transfer area in the reactor.

Example 3

Lift tubes were employed to demonstrate the operability of continuous catalyst rejuvenation during the same set of runs used to demonstrate the efficacy of such tubes for catalyst redistribution using the same apparatus described in Example 2. The rejuvenation tubes, however, are separate, distinct, and independent of the four previously described draft tubes and are tubes used in addition to the previously described draft tubes. The rejuvenation tubes are pipes 3" in diameter and 31 to 32 feet long.

Figure 5A:
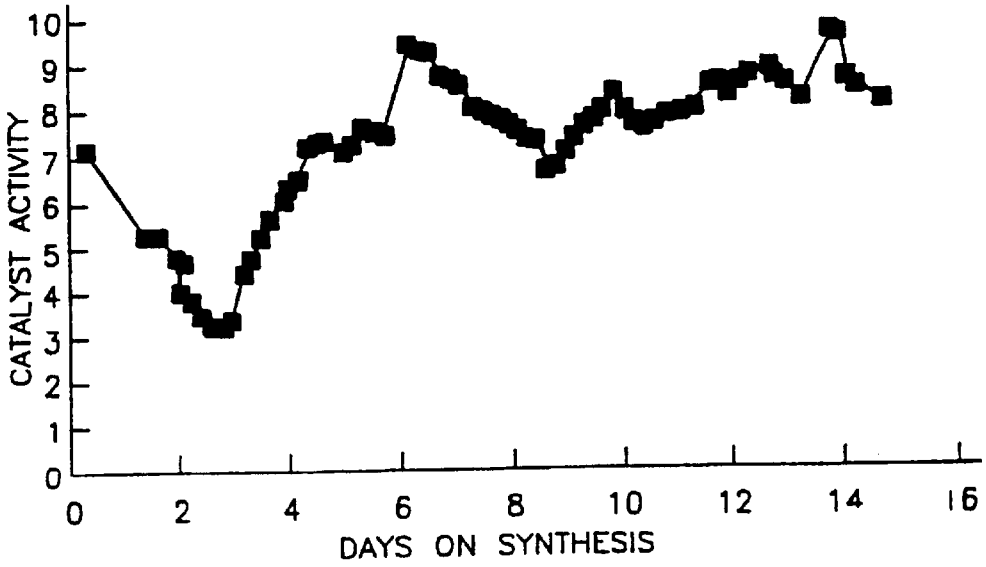
FIG. 5A presents catalyst activity and FIG. 5B shows hydrogen flow rates in continuous catalyst rejuvenation.
Figure 5B:
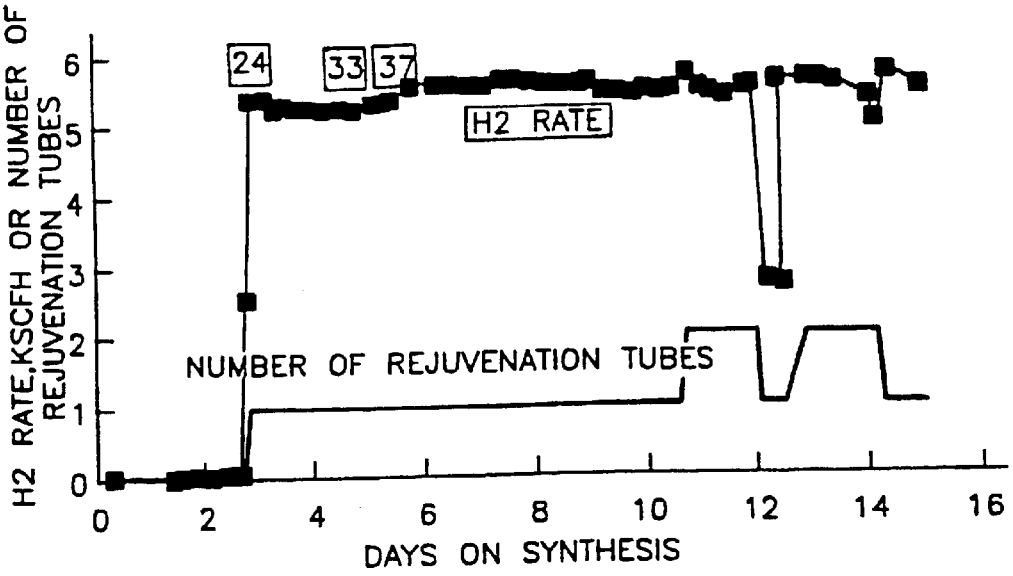

FIG. 5A illustrates the good results obtained with continuous hydrogen rejuvenation using generally one rejuvenation tube, but never more than two tubes. The numbers in boxes on the figure are material balance serial numbers. The upper plot, FIG. 5A shows, between day 0 and day 3, the typical rapid catalyst deactivation that occurred in the hydrocarbon synthesis reactor. FIG. 5B shows the number of rejuvenator tubes used and the hydrogen flow rate. At about day 3, hydrogen was fed to one rejuvenation tube, first in the amount of about 2.5 kscfh and then at about 5.5 kscfh (superficial gas velocity 37 cm/sec and 76 cm/sec). As soon as the hydrogen gas was started to the rejuvenator tubes, not only did the catalyst activity cease to decline but it immediately began to climb sharply. Although the activity varied somewhat during the rest of the run, depending upon what other experiments were being carried out (see Example 2), the catalyst activity remained at or near its maximum value, thereby demonstrating the efficacy of continuous rejuvenation.

Figure 6A:
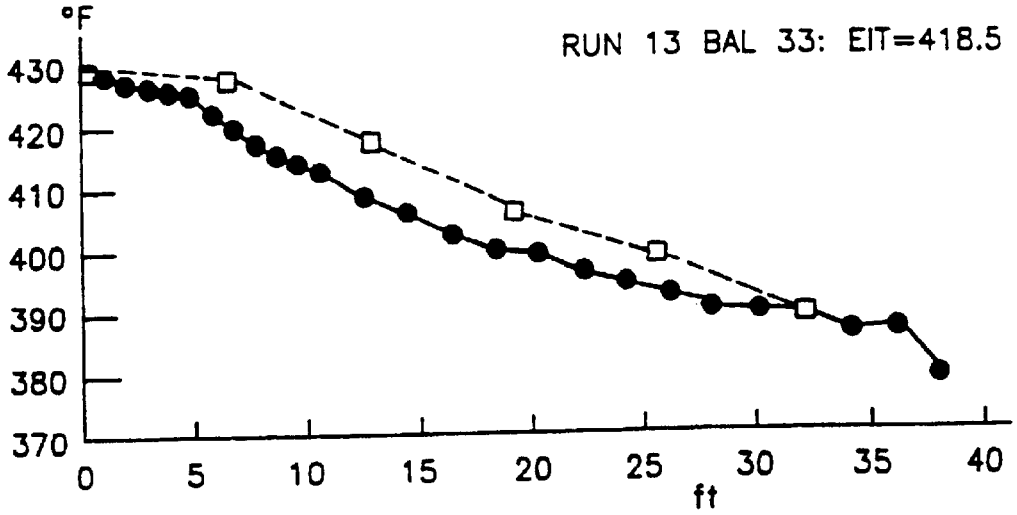
FIGS. 6A, B and C present three pairs of temperature profiles comparing temperatures inside the rejuvenator tube with temperature in the reactor slurry outside the rejuvenator tube at different temperatures in the reactor slurry.

The extent of the rejuvenation reaction occurring in the continuous rejuvenation experiment was monitored by thermocouples placed inside one of the rejuvenation tubes. The measured temperature profile in the rejuvenation tube is compared with the temperature profile in the reactor slurry surrounding the rejuvenation tube for three different balances in FIGS. 6(A–C). In FIGS. 6(A–C), the solid circles represent the axial temperature profile in the reactor slurry, while the open squares represent the axial temperature profile in the rejuvenation tube. In all three plots of FIGS. 6(A–C), the abscissae represents the axial distance in feet above the bottom of the reactor, and the ordinate represents temperature in degrees Fahrenheit. The difference in temperature between the rejuvenation tube and the reactor slurry is the temperature rise in the rejuvenation tube, which is a measure of the extent of the rejuvenation reaction occurring there. A comparison of the top two plots (FIGS. 6A & B) shows the effect of the temperature level upon the extent of reaction occurring in the rejuvenation tube for two balances that were close to one another in time. Balance 37, made at an average temperature in the reactor of 428.5° F., showed a considerably greater temperature rise in the rejuvenation tube than was exhibited in Balance 33 made at an average reactor temperature of 418.5° F. Thus, the efficacy of continuous rejuvenation depends upon the temperature level in the rejuvenation tube, which in these experiments was controlled by the temperature in the reactor slurry itself. Monitoring temperature in the reactor and temperature rise in the rejuvenator tube is an efficient method for monitoring catalyst rejuvenation. This temperature rise increased as the amount of rejuvenation that occurred in the rejuvenation tube increased.

Figure 6B:
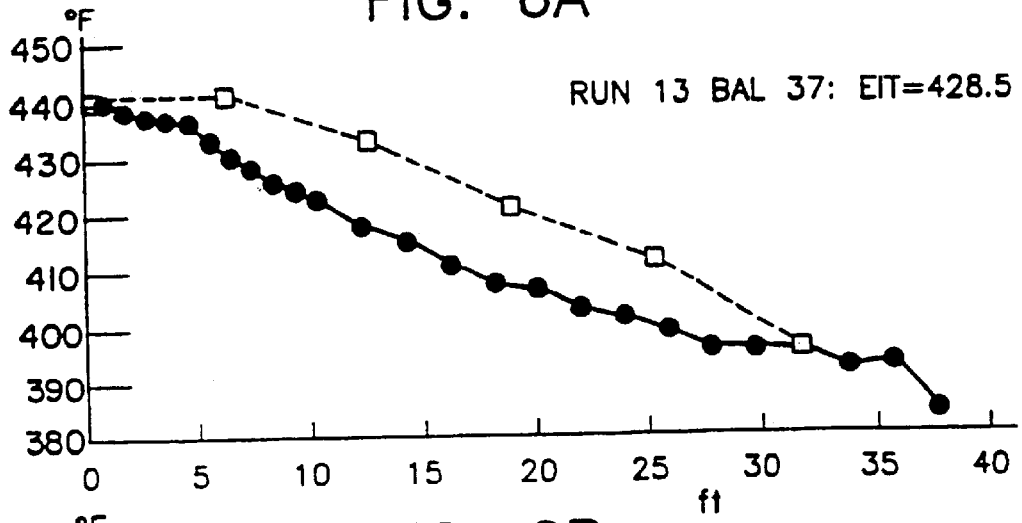
Figure 6C:
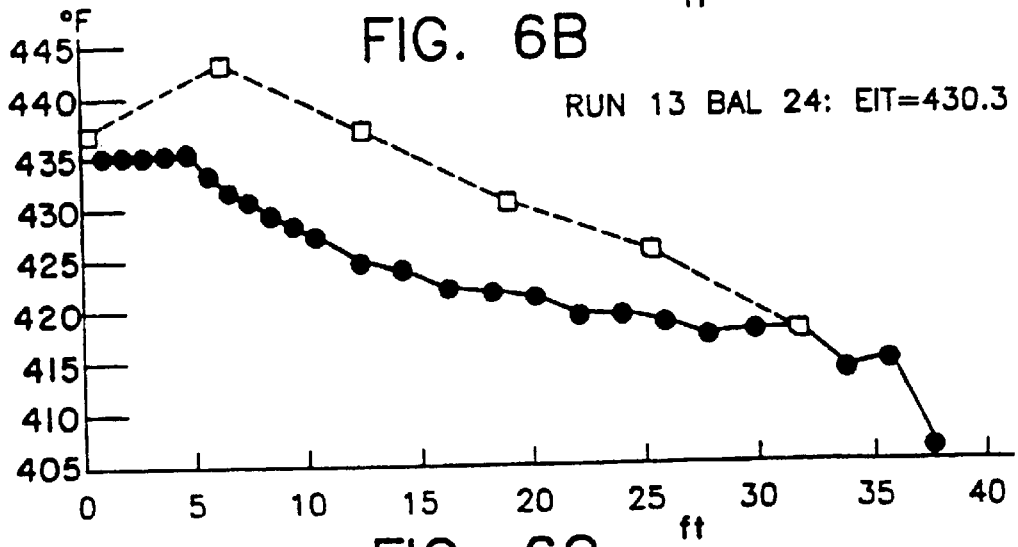

A comparison of the bottom two plots in FIGS. 6B & C demonstrate that the condition of the wax in the reactor also affects the extent of reaction occurring in the rejuvenation tube. Balance 24, made at 3.2 days on synthesis, occurred at the beginning of the continuous rejuvenation experiment. Hence, for this balance, catalyst activity was low being 4.3 (see FIG. 5 at day 3.2) indicating that the concentration of the deactivating species in the wax and on the catalyst was high, and the amount of reaction that occurred in the rejuvenation tube was also high, as attested by the temperature rise in the rejuvenation tube. For Balance 37 made at 5.43 days on synthesis, on the other hand, for which the reactor temperature was very similar to that for Balance 24 (428.5° F. vs. 430.3° F.) but for which the catalyst activity was near its maximum being 7.6, indicating that the level of deactivants in the wax and on the catalyst was low, the temperature rise in the rejuvenation tube was lower than that for Balance 24. Thus, both wax condition and temperature level in the rejuvenation tube were important in determining the amount of the cleansing, rejuvenation reaction that occurred in continuous rejuvenation.

The gas rate to the rejuvenation tubes, which determines the residence time of the reactor slurry in the tubes, was also found to be important in determining the efficacy of the rejuvenation. Referring again to FIGS. 5A & B, between days 10 and 11, rejuvenation was carried out in both one and two rejuvenation tubes. While activity was declining with only one rejuvenation tube in service, activity again increased when the second tube was put in service, even though the total amount of hydrogen being fed to the two rejuvenation tubes was held constant. These data showed the importance of controlling the residence time of the fluids in the rejuvenation tube by controlling the amount of hydrogen rejuvenation gas being fed to the tube. Rejuvenation time will, of course, be dependent on the degree of catalyst deactivation as well as rejuvenator tube diameter, and is within the control of the practitioner. Too high a rate of hydrogen flow reduced the residence time in the tube to the point that insufficient time was available for the pre-cleanup and cleanup reactions to occur.

Reference to Table I reveals that even when only 1 rejuvenation tube of 3" diameter with hydrogen gas passing through it at 74.8 cm/sec. was in operation there was a noticeable degree of improvement in catalyst circulation, Balances 47 and 58. During the period that there was no lift gas fed to the four lift tubes described in Example 2, but one rejuvenation tube of 3" diameter was being used which employed $H_2$ at about 72 cm/sec. superficial space velocity the catalyst distribution in the vessel, as reflected by catalyst density measured at different heights in the vessel, improved. This demonstrates, therefore that catalyst rejuvenation and improved catalyst distribution can be achieved in a single operation using the same tubes as both catalyst distribution and rejuvenation tubes when $H_2$ is used as the lifting gas.

Example 4

The following example gives the physical configuration and the beneficial effects obtained from a rejuvenation tube that has external insulation and internal heating or cooling. The advantage is that the effectiveness of continuous catalyst rejuvenation can be controlled independently of temperature in the reactor.

Prior to Fun 16 of the hydrocarbon synthesis pilot demonstration unit (HCS-PDU), the rejuvenation tube was altered by providing (1) an external jacket for heat insulation and (2) an internal tube to provide either heating or cooling. Specifically, the rejuvenation tube was a nominal 3-inch diameter pipe 46' in length. Attached concentrically to the outside of this rejuvenation pipe was a nominal 4-inch diameter pipe also 46' in length whose purpose was to reduce the rate of heat transfer between the rejuvenation pipe and the reactor slurry. The ends of the 4-inch pipe were sealed against the 3-inch pipe so that the gap between them served as a heat transfer barrier. Inside the 3-inch rejuvenation pipe and concentric with it was placed a nominal 1-inch pipe the bottom of which was sealed. This pipe extended the length of and extended out of the top of the 3" pipe and ended in a "T" fitting. This 1-inch pipe could be heated or cooled with steam to control the temperature of the fluid inside the rejuvenation pipe independently of the temperature in the reactor. Steam was supplied to the upper end of the 1-inch pipe through the horizontal arm of the "T" fitting. Inside the 1-inch pipe and concentric with it was placed a length of ¾-inch tubing that extended to length of the 1 inch pipe and extended out of the top of the "T" and exited into a steam trap. The purpose of this tubing was to provide an outlet for the condensate accumulating in the 1-inch pipe in the event the 1-inch pipe was used for heating or to provide an outlet for the exit steam in the event the 1-inch pipe was used for cooling. The lower end of the 1-inch pipe was outfitted with six fins to increase the transfer of heat to the incoming liquid-catalyst slurry. Each fin was ¼" thick, ½" wide, and 8' long. The lower end of the rejuvenation pipe was baffled to prevent, as much as possible, influx of reactant gases with the liquid-catalyst slurry into the lower end of the rejuvenation tube.

The following data show the benefit for heating the rejuvenation tube by comparing the rate of change in conversion in the reactor with time brought about by adding steam to heat the rejuvenation tube contents. During the period of these tests, all other conditions of feed rate, feed composition, temperature, and slurry height were kept essentially constant. The results are given in the table below.

Benefit of Adding Heat During Continuous Rejuvenation

| Heat Addition | No | Yes |
|---|---|---|
| HCS-PDU Run 16 Balance Periods | 19–23 | 24–35 |
| Rejuvenation Gas Rate, KSCFH | 5.1 | 4.8 |
| Average Reactor Temperature, ° F. | 427.7 | 427.3 |
| Average Temperature in Rejuvenation Tube, ° F. | 429.9 | 439.6 |
| CO Conversion Range, % | 32–26 | 26–36 |
| Conversion Change/Day | −12.4 | +10.4 |

In this run of the hydrocarbon synthesis pilot demonstration unit, five balances (19–23) were made in which catalyst-wax slurry was pumped through the rejuvenation tube using pure $H_2$ as the rejuvenation and lift gas with no steam being added to the 1-inch pipe. The average temperature in the rejuvenation tube was 429.9° F. compared with an average reactor temperature of 427.7° F. The CO conversion during this period dropped from 32 to 26% over the period of about a half day, giving a rate of change in conversion of −12.4% conversion/day. The degree of catalyst rejuvenation occurring was inadequate to maintain a constant catalyst activity.

Then, over the next 12 balance periods, while keeping the rejuvenation gas rate nearly constant, high pressure steam was added to the 1-inch pipe through the horizontal arm of the "T" fitting to help heat the contents of the wax-catalyst slurry being contacted in the rejuvenation tube with the hydrogen. The average temperature in the rejuvenation tube during this period was 439.6° F. in the rejuvenation tube compared with an average temperature of 427.3° F. in the reactor. Over about a 24-hour period, the conversion increased from 26 to 36%, giving a rate of change in conversion of +10.4% conversion/day. Thus, by being able to increase the temperature inside the rejuvenation tube just about 10°–12° F. independently of the temperature in the reactor itself, catalyst rejuvenation was increased to the point that not only did the conversion stop falling but rather it was increasing at a rapid rate.

These data confirm the earlier data presented in Example 3 that demonstrated the improvement in catalyst rejuvenation brought about by performing the rejuvenation in the rejuvenation tube at a temperature higher than that of the surrounding reactor. The data presented here support the invention that by insulating the rejuvenation tube and providing internal heating, the rejuvenation rate can be controlled independently of the reactor temperature.

What is claimed is:

1. A method for rejuvenating reversibly deactivated particulate hydrocarbon synthesis catalyst in a slurry phase reactor, said method comprising the use of substantially vertical draft tube means, open at both ends, fully immersed in the slurry containing the catalyst and injecting a hydrogen containing gas at or substantially near the bottom of said draft tube means thereby lifting catalyst in slurry from the bottom of the slurry phase reactor into and through the open bottom end of the draft tube means, rejuvenating catalyst in the presence of said hydrogen containing gas in the vertical draft tube means and ejecting the rejuvenated catalyst into the top of the slurry phase in the slurry phase reactor through the open top of the draft tube means.

2. The method of claim 1 wherein the cross sectional surface area of the draft tube means occupies from 0.2 to 10% of the cross sectional surface area of the slurry phase reactor.

3. The method of claim 1 wherein the substantially vertical draft tube means comprises one or more individual draft tubes.

4. The method of claim 3 wherein when multiple draft tube means are employed no single draft tube constitutes more than 50% of the total cross sectional area of the total draft tube means.

5. The method of claim 3 wherein the individual draft tube means of the draft tube means possess a diameter such that a sufficiently lower slurry density is maintained in the draft tubes than in the surrounding slurry in the reactor vessel.

6. The method of claim 1 wherein the open bottom end of the draft tube means is located at a height of from 0.1 to 1 foot above the bottom of the slurry phase reactor.

7. The method of claim 1 wherein the hydrogen containing gas is injected into the substantially vertical draft tube means at a rate such that the superficial gas velocity in the draft tube means is at least 0.2 to 40 times the superficial gas velocity of the gases in the slurry phase reactor thereby permitting sufficient residence time in the draft tube means for catalyst regeneration - rejuvenation to occur.

8. The method of claim 1 wherein the bottom end of the substantially vertical draft tube means is fitted with gas deflecting means to minimize entry of reactant gases into the draft tube means.

*9. A method for producing hydrocarbons in a slurry phase reactor utilizing a hydrocarbon synthesis catalyst which comprises rejuvenating said hydrocarbon synthesis catalyst in accordance with the method of claim 1.*

*10. The method of claim 9 wherein said slurry comprises the product of said hydrocarbon synthesis including* $C_{5+}$ *hydrocarbons.*

*11. The method of claim 10 wherein said slurry comprises* $C_5$–$C_{100}$ *hydrocarbons.*

*12. The method of claim 11 wherein said slurry comprises Fischer-Tropsch waxes.*

*13. The method of claim 9 wherein said hydrocarbon synthesis catalyst comprises a Fischer-Tropsch catalyst.*

*14. The method of claim 13 wherein said Fischer-Tropsch catalyst comprises a Group VIII metal selected from the group consisting of iron and cobalt.*

* * * * *